United States Patent [19]

Reeve et al.

[11] Patent Number: 5,670,346

[45] Date of Patent: Sep. 23, 1997

[54] MODIFYING NUCLEOTIDE ANALOGUES

[75] Inventors: Michael Alan Reeve, Henley-on-Thames; Philip Steven Robinson, Aylesbury, both of United Kingdom

[73] Assignee: Amersham International plc, Buckinghamshire, United Kingdom

[21] Appl. No.: 399,582

[22] Filed: Mar. 7, 1995

[30] Foreign Application Priority Data

Mar. 8, 1994 [EP] European Pat. Off. .............. 94301636

[51] Int. Cl.$^6$ .............. C12P 19/34; C12P 19/30; C12N 15/10

[52] U.S. Cl. .............. 435/91.53; 435/6; 435/21; 435/89; 435/91.1; 435/91.2; 210/632; 935/77; 935/78

[58] Field of Search .............. 435/6, 21, 89, 435/91.1, 91.2, 91.53; 210/632; 935/77, 78

[56] References Cited

FOREIGN PATENT DOCUMENTS

WO93/06243 1/1993 WIPO.
WO93/24655 12/1993 WIPO.

OTHER PUBLICATIONS

Short Protocols in Molecular Biology, Ausubel et al. eds., pp. 2–4 to 2–7, 1992.
Wallace, Methods in enzymology 152:41–48 (1987).
V. Rao, *Analytical Biochemistry*, vol. 216, No. 1, pp. 1–14 (1994).

*Primary Examiner*—Jean C. Witz
*Assistant Examiner*—Francisco C. Prats
*Attorney, Agent, or Firm*—Wenderoth, Lind & Ponack

[57] ABSTRACT

Fluorescently labelled dideoxynucleoside triphosphates are widely used as chain-terminators in Sanger dideoxy sequencing operations. But these unincorporated dye-terminators migrate in an electrophoresis gel and obscure the desired sequence ladder. This invention provides a method and a kit for modifying the unincorporated dye-terminators, e.g. by removal of a 5'-triphosphate group by chemical or enzymatic means e.g. by use of a phosphatase enzyme.

8 Claims, 4 Drawing Sheets

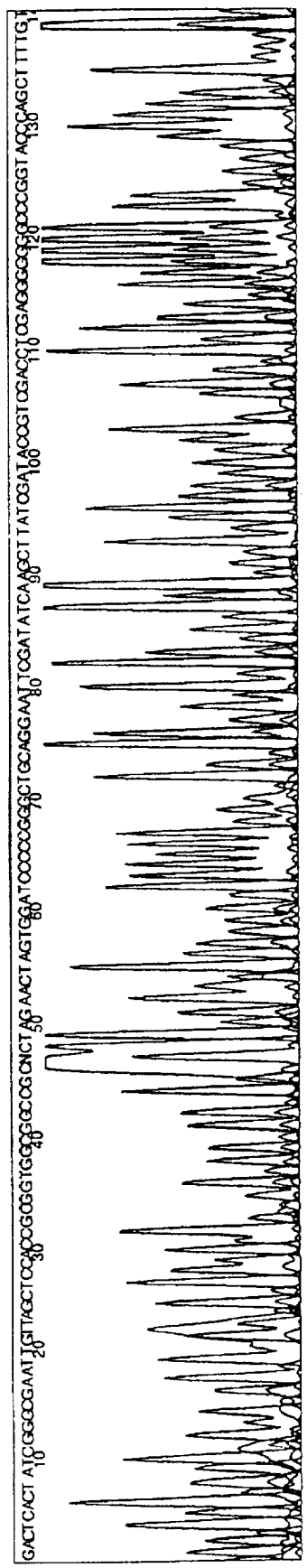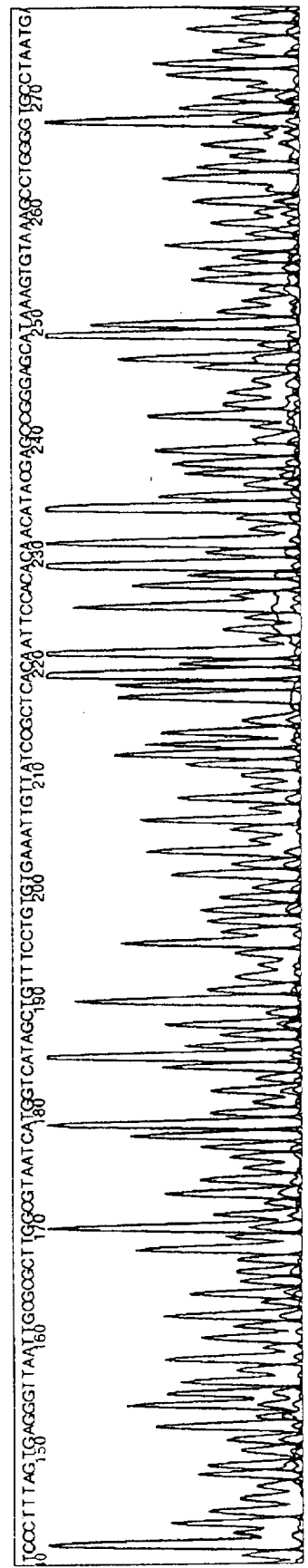

MODIFYING NUCLEOTIDE ANALOGUES

Fluorescently labelled dideoxynucleoside triphosphates (hereafter referred to as dye-terminators) have found widespread usage in DNA sequencing applications, DNA mapping applications and DNA labelling applications. These dideoxynucleoside triphosphate analogues can be incorporated in a base-specific manner onto the 3' end of a growing DNA chain with the aid of a suitable polymerase and buffer system.

As dye-terminators lack 3' hydroxyl groups, incorporation of such residues gives rise to DNA chains that can no longer be extended by means of the polymerase.

For example, in DNA sequencing applications, four different fluorophores are attached to ddATP, ddCTP, ddGTP and ddTTP respectively. Each of the (dye-terminator) dideoxy chain terminated products in a nested set originating from a primer will be characterised by a particular terminal base-specific fluorophore (and hence fluorescence emission wavelength under appropriate excitation conditions). Polyacrylamide gel electrophoresis of the nested set of such chain termination products can be coupled to fluorescence excitation and detection in order to call the sequence of bases from a particular DNA sample. (See WO 91/05060, herein incorporated by reference).

In practice the fluorophores attached to ddATP, ddCTP, ddGTP and ddTTP each imparts a small perturbation in the rate of migration of the nested set of chain termination products through polyacrylamide gels. This problem is easily overcome with the use of appropriate mobility correction algorithms.

Commercially available dye-terminators currently exist for both Sequenase and Ampli Taq DNA polymerases.

DISADVANTAGES OF THE CURRENT ART

One of the major drawbacks to the elegant applications in which dye-terminators can be employed concerns the removal of residual (unincorporated) dye-terminators after the base-specific incorporation of dye-terminators is complete. Residual (unincorporated) dye-terminators are intensely fluorescent and, for example, migrate within several regions of polyacrylamide sequencing gels in which fluorescent chain terminated fragments of interest are to be found. The residual (unincorporated) dye-terminators thus interfere with the base calling in these regions of the sequence.

In order to avoid problems such as the above, much effort needs to be invested in the removal of these residual (unincorporated) dye-terminators.

Current methods rely upon selective alcohol precipitation, phenol extraction, CTAB precipitation or column chromatography in order to remove residual (unincorporated) dye-terminators. (See, for example ABI User Bulletin 20, December 1991 herein incorporated by reference).

None of the above methods are particularly robust and all are both time consuming and difficult to automate.

Similar problems may arise when the chain-terminating nucleotide analogues are radioactively or otherwise labelled. Even unlabelled chain-terminating nucleotide analogues may be a nuisance during electrophoresis for sequencing purposes. Similar problems can also arise where labelled nucleotides or nucleotide analogues (other than chain-terminating nucleotide analogues) are used for incorporation in a growing DNA chain.

The present invention addresses all these problems. In preferred embodiments it is both rapid and robust and is particularly suited to automation.

THE INVENTION

In one aspect the invention provides a method of treating a solution containing one or more fluorescently-labelled nucleotides or analogues and DNA chains incorporating residues of the one or more fluorescently-labelled nucleotides or analogues, which method comprises modifying the one or more fluorescently-labelled nucleotides or analogues without correspondingly modifying the residues of the one or more fluorescently-labelled nucleotides or analogues incorporated in the DNA chains.

In another aspect the invention provides a kit comprising:
a) a supply of nucleotides or analogues,
b) a polymerase enzyme,
c) a supply of one or more chain-terminating nucleotide analogues, either component a) or component c) being fluorescently labelled, and
d) means for modifying at the 5'-position the nucleotides and/or nucleotide analogues.

The solution to be treated may typically be a solution destined to be applied to an electrophoresis gel as part of a standard sequencing or mapping operation. A nucleotide analogue is a chemical entity which is capable of being incorporated in a nucleic acid chain by means of a polymerase enzyme under base-specific pairing conditions.

The one or more nucleotides or analogues to be modified are fluorescently-labelled, i.e. labelled with a moiety which emits fluorescence when illuminated with light of suitable wavelength. Usually unlabelled nucleotides or analogues will also be present.

The one or more fluorescently-labelled nucleotides or analogues to be modified may lack a 3'-hydroxyl group, by virtue of which they are usually chain-terminators. Examples are 3'-fluoro and 3'-azido nucleoside triphosphates. Of particular importance in connection with Sanger sequencing are 2', 3'-dideoxynucleoside triphosphates. The method of this invention is expected to be useful when at least one chain-terminating nucleotide analogue is fluorescently labelled, and particularly when four chain-terminating nucleotides are labelled each with a different fluorescent label.

In other circumstances, there may be present one or more fluorescently-labelled nucleotide analogues which are incorporated in growing nucleic acid chains without acting as chain-terminators. These can also be subject to modification as described below.

All these fluorescently-labelled nucleotides or analogues have a 5'-triphosphate group which is negatively charged. This negative charge is partly responsible for their undesired migration during electrophoresis. The modification of the invention preferably involves removal of one, two or preferably three phosphate moieties of this triphosphate group. Removal can readily be effected enzymatically, e.g. by the use of a phosphatase enzyme such as alkaline phosphatase. Acid phosphatase has also been used with success. Alternatively, partial or complete removal of the triphosphate group can be effected by chemical techniques. Alternatively again, the triphosphate group can be altered, rather than removed, in such a way that the modified nucleotide or analogue migrates through an electrophoresis gel at a different rate.

It is found in practice that the use of a phosphatase enzyme in this way overcomes the problem of interference by residual unincorporated dye-terminators with the base calling at regions of a sequencing gel. It is not certain whether this effect results from the partial or complete removal of phosphate moieties of the 5'-triphosphate groups of the dye terminators. Probably unincorporated dye-

3 terminators with a 5'-monophosphate group or a 5'-hydroxyl group do not interfere while those with a 5'-diphosphate group may cause slight interference.

Nucleotides or analogues which have been incorporated in a growing DNA chain do not have such 5'-triphosphate groups. The mobility of these moieties is governed by the nature of the DNA chain to which they are attached. This DNA chain may typically have a 5'-hydroxyl group, derived from a chemically synthesised oligodeoxyribonucleotide primer used to prime a nested set of polymerase catalysed DNA chains. At the 3'-end of each chain is the residue of a chain-terminating nucleotide or analogue. Enzymatic or chemical treatment as described above will have no effect on the nested set of DNA chains or on their electrophoretic mobility. Enzymatic or chemical treatment as specified will thus result in alteration of the mobility of any free nucleotides or analogues present, without correspondingly altering the mobility of DNA chains containing residues of those nucleotides or analogues. Thus after the enzymatic or chemical treatment specified, the treated solution can if desired be subjected to electrophoresis in agarose, polyacrylamide, hydrolink or other electrophoretic gel or matrix, for sequencing or other purposes. Alternatively, other forms of separation are known and are possible.

It may however be preferred to remove fluorescently-labelled nucleotides or nucleosides or analogues which have not become incorporated in growing DNA chains, prior to subjecting the solution to electrophoresis. The enzymatic or chemical treatment specified above may modify the nucleotides or analogues in such a way as to make their removal from the solution easier. These modified nucleotides or nucleosides or analogues behave differently with respect for example to selective alcohol precipitation, CTAB precipitation, phenol extraction and column chromatography. For example, reduction of non-specific binding of nucleotides or nucleosides or analogues to magnetic beads has many advantages in the automation of DNA sequencing protocols.

It will often be preferred to subject the treated solution to alcohol precipitation. This treatment has the effect of concentrating the DNA, which comes down in the precipitate, removing salt, and removing at least part of the unincorporated nucleotides or analogues. The modified nucleotides or nucleosides or analogues, which result from the phosphatase enzyme treatment described, have a greater tendency (than do the unmodified nucleotides or analogues) to remain in solution. Hence the phosphatase enzyme treatment described enhances the effectiveness of a subsequent alcohol precipitation step.

A kit according to the invention includes standard ingredients, namely a) a supply of nucleotides or analogues generally all four nucleotides; b) a supply of a polymerase enzyme; and c) a supply of one or more chain-terminating nucleotide analogues. Either component a) or component c), most usually component c) is fluorescently labelled. In addition, the kit comprises d) means for modifying at the 5'-position the unincorporated nucleotides and/or nucleotide analogues e.g. present in a sequencing solution. This means may suitably be a phosphatase enzyme such as alkaline phosphatase.

BRIEF DESCRIPTION OF THE DRAWINGS

FIGS. 1A-1D is a trace fluorescent signals against chain of a sequencing product which was treated with alkaline phosphatase.

4

EXPERIMENTAL

Example 1

Demonstration of the modification of the Electrophoretic mobility of dye-terminators using alkaline phosphatase The commercially available ABI Amplitaq dye-terminator kit was used to set up 5 cycle sequencing reactions. The reactions were set up as laid out in the product protocol booklet. The template used was 1 µg of M13 mp8, purified by centrifugation in a cesium chloride gradient. The primer used was 1.0 pmol of M13 Universal primer. Samples were overlaid with 50 µl of light mineral oil and thermal cycled using the protocol as below.

Pre-denaturation at 93° C. for 5 mins followed by 25 cycles of:

Annealing at 50° C. for 15 secs, extension at 60° C. for 4 mins, and denaturation at 95° C. for 30 secs.

Samples were recovered from under the oil overlay post-sequencing and Nos. 2–5 were subjected to calf intestinal alkaline phosphatase digestion at 10, 5, 2.5 and 1 µl respectively. Digestion was carried out for 5 mins at 37° C. No. 1 was subjected to identical treatment without alkaline phosphatase. Post-digestion, the samples were diluted with an equal volume of glycerol, and loaded onto a pre-formed 1% agarose gel. Gel-Electrophoresis was carried out for 30 mins at 200 mA, 200 V. The products were visualised by means of a UV transilluminator. The resulting photograph was taken using Polaroid 667 film at f 5.6 for 1 sec.

The photograph of the gel (not reproduced here) demonstrates conclusively that unmodified dye-terminators migrate into the gel (Track 1), showing that they possess a net negative charge, whereas the alkaline phosphatase digested dye-terminators do not migrate into the gel, indeed they migrate slightly towards the –ve charged electrode, demonstrating that they now possess a slight +ve charge, due to removal of the 5' triphosphate group.

Example 2

Figure 1C:
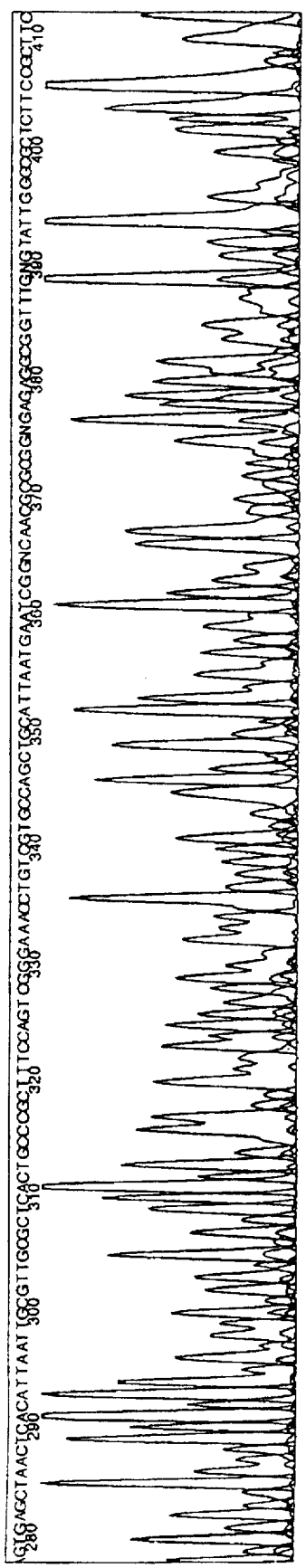
Figure 1D:
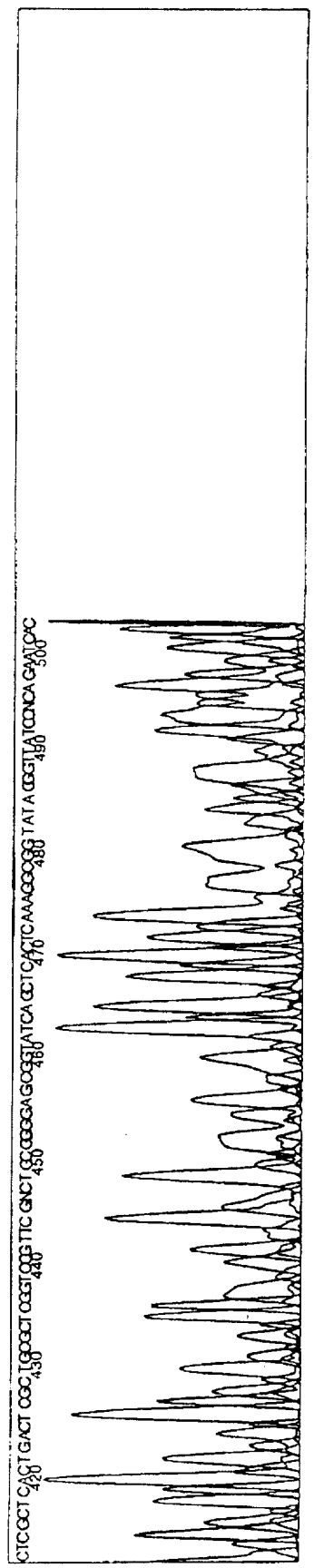
Figure 2A:
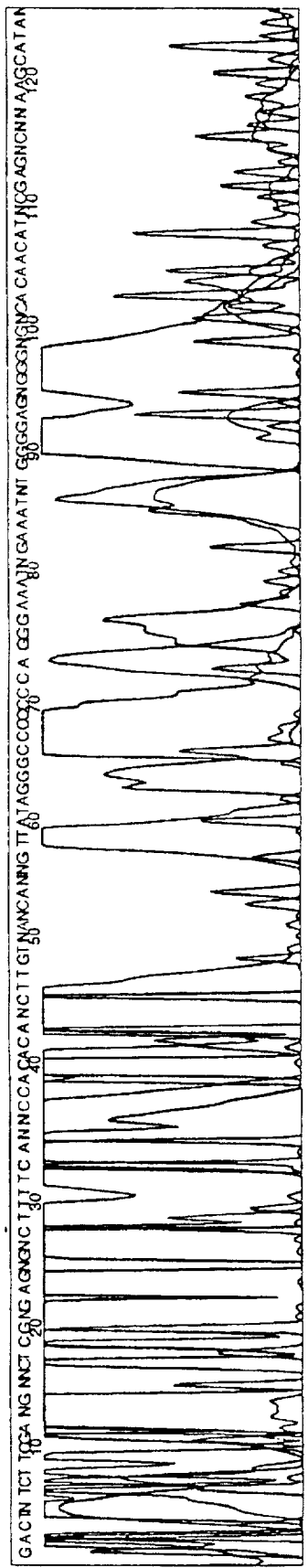
FIGS. 2A-2D is a trace of fluorescent signals against chain length of a sequencing product which was not treated with alkaline phosphatase.
Figure 2B:
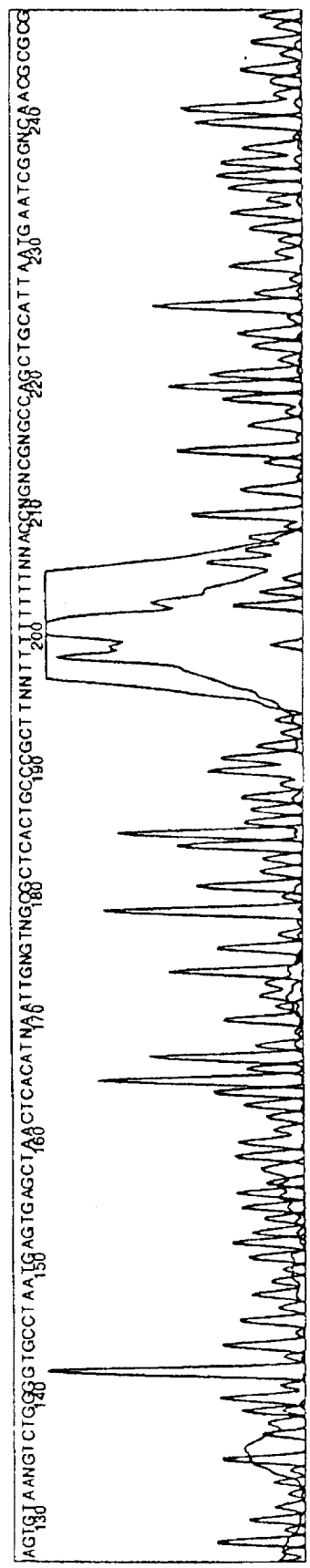
Figure 2C:
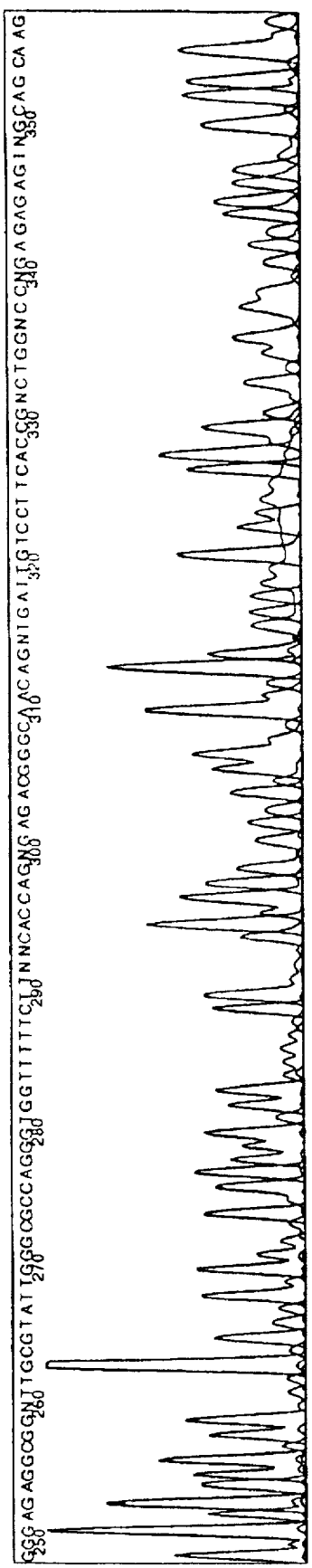
Figure 2D:
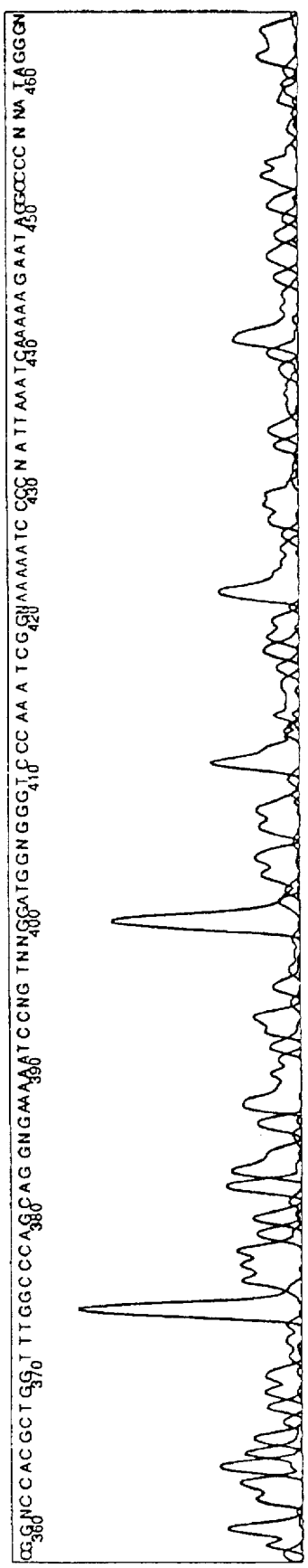

Demonstration of removal of dye-terminator artefacts by the use of alkaline phosphatase Two Amplitaq generated sequence ladders were set up as outlined in Example 1. One was subjected to alkaline phosphatase treatment again as outlined previously. The other remained untreated. Both samples were then ethanol precipitated by adding ×0.5 vol of 7.5M ammonium acetate (10 µl) and ×2.5 vol of fast magnetic purification particles in ethanol (100 µl at 0.5 mg/ml particles). The precipitations were then allowed to go to completion for 30 mins at room temperature. The particles were then recovered from the solution by the addition of a magnetic field and the supernatants removed by vacuum aspiration. The recovered particles were washed in 500 µl of ethanol, separated by magnetic field addition and the supernatant again removed. This washing step was repeated once more and repeated finally with the addition of 70% ethanol, as opposed to 100% ethanol. The particles were then resuspended in 30 µl of 0.8 mM EDTA, 8% formamide. The sequences generated having dissolved in the aforementioned solution were separated from the particles by addition of the magnetic field, and transferred to a fresh tube. These samples were then concentrated to 3 µl in a Savant vacuum centrifuge, denatured at 92° C. for 2 mins and loaded onto a 6% polyacrylamide gel on an ABI 373A DNA sequencer. The sequencer was run for 12 hours and the resulting two traces were generated using the Analysis software on the machine. The traces are reproduced in FIGS. 1 and 2. FIG. 1 is the trace obtained with alkaline phosphatase treatment. FIG. 2 is the trace obtained without alkaline phosphatase treatment.

Each figure is a trace of four different fluorescent signals (which are distinguished by colour in the original) against chain length obtained using commercial equipment operated under the recommended conditions. The chain length and the identity of each 3'-terminal nucleotide is indicated above the trace.

As can be seen from the traces the treatment of the generated sequence ladders with alkaline phosphatase causes removal of the dye-terminator artefacts, and allows for accurate base calling with the ABI analysis software (FIG. 1). The untreated control sample produced a sequence that was readable only in parts, with other parts (e.g. the regions 0–100 and 190–210) being obscured by unincorporated dye-labelled nucleotide analogues, demonstrating well the problems of dye-terminator artefacts electrophoresing in the area of the sequence ladders (FIG. 2).

We claim:

1. A method of treating the product of a nucleic acid sequencing, mapping or labelling reaction containing one or more fluorescently-labeled nucleotides or analogues and DNA chains incorporating residues of the one or more fluorescently-labelled nucleotides or analogues to reduce the interference of unincorporated fluorescently-labelled nucleotides or analogues, which method comprises using an enzyme to remove at least one 5'-phosphate group of the one or more fluorescently-labelled nucleotides or analogues without correspondingly modifying the residues of the one or more fluorescently-labelled nucleotides or analogues incorporated in the DNA chains and then subjecting the treated product to gel electrophoresis.

2. The method as claimed in claim 1, wherein the one or more fluorescently-labelled nucleotides or analogues lack a 3'-OH group.

3. The method as claimed in claim 2, wherein the one or more fluorescently-labelled nucleotides or analogues are 2',3'-dideoxynucleoside triphosphates.

4. The method as claimed in claim 1, wherein the enzyme is a phosphatase enzyme.

5. The method as claimed in claim 4, wherein the phosphatase enzyme is an alkaline phosphatase.

6. The method as claimed in claim 5, wherein the enzyme is used to remove a 5'-triphosphate group of the one or more fluorescently-labelled nucleotides or analogues.

7. The method as claimed in claim 1, wherein the treated product is run on an electrophoresis sequencing gel.

8. The method as claimed in claim 1, wherein before gel electrophoresis the treated product is subjected to alcohol precipitation to concentrate and purify the DNA chains.

* * * * *